United States Patent [19]

Rand

[11] Patent Number: 4,979,898

[45] Date of Patent: Dec. 25, 1990

[54] MEASURING INSTRUMENTS PARTICULARLY USEFUL AS DENTAL IMPLEMENTS

[76] Inventor: Abraham Rand, 100 Neve Aliza, Ginot Shomron, Israel

[21] Appl. No.: 337,674

[22] Filed: Apr. 13, 1989

[51] Int. Cl.$^5$ .............................................. A61C 19/04
[52] U.S. Cl. .......................................... 433/72; 33/513
[58] Field of Search .................. 433/72, 75; 33/513, 33/514, 832, 836; 128/776, 777

[56] References Cited

U.S. PATENT DOCUMENTS

| | | | |
|---|---|---|---|
| 2,787,837 | 4/1957 | Gelfand | 33/514 |
| 3,058,225 | 10/1962 | Ward | 33/513 |
| 3,559,292 | 2/1971 | Weissman | 33/514 |
| 4,289,382 | 9/1981 | Clark | 33/832 |
| 4,470,810 | 9/1984 | Bourdeau et al. | 433/72 |
| 4,764,114 | 8/1988 | Jeffcoat et al. | 433/72 |
| 4,765,064 | 8/1988 | Maeda | 33/832 |
| 4,791,940 | 12/1988 | Hirschfeld et al. | 33/513 |
| 4,841,987 | 6/1989 | Brown et al. | 33/514 |

Primary Examiner—John J. Wilson
Attorney, Agent, or Firm—Benjamin J. Barish

[57] ABSTRACT

Two small portable measuring instruments, particularly useful as dental implements, comprises a housing, a stem displaceable within a bore in the housing, a fingerpiece coupled to one end of the stem and engageable by the user for displacing the stem, the opposite end of the stem being displaceable through an opening in the housing, an electrical measuring circuit for measuring the displacement of the stem, and a display for displaying the displacement of the stem. One embodiment, is described wherein the instrument is used as a dental probe for measuring the depth of a dental pocket, and a second embodiment is described wherein the instrument is used to measure the mobility of a tooth.

17 Claims, 1 Drawing Sheet

MEASURING INSTRUMENTS PARTICULARLY USEFUL AS DENTAL IMPLEMENTS

BACKGROUND OF THE INVENTION

The present invention relates to measuring instruments. The invention is especially useful as dental implements for making various dental measurements, particularly for measuring the depth of a dental pocket and/or for measuring the mobility of a tooth, and the invention is therefore described below with respect to these applications.

One form of measurement widely made by dentists is the depth of gingival and periodontal pockets. For this purpose, the dentist frequently uses a conventional dental probe, namely, a slender metal rod having a handle at one end, and a tapered tip graduated in millimeters at the opposite end. However, it is difficult to make and read accurate measurements when using the conventional dental probe.

Another measurement frequently made by dentists is the mobility of a tooth, i.e., the movement of the tooth primarily in the horizontal direction when a force (e.g., finger pressure) is applied. This measurement is usually made by the dentist by pressing a finger against the tooth to force it to move, but this produces a very inaccurate and subjective measurement.

OBJECTS AND SUMMARY OF THE INVENTION

An object of the present invention is to provide a measuring instrument, particularly useful as a dental implement, permitting accurate dental measurements to be made and read.

According to the present invention, there is provided a small, portable measuring instrument, which is particularly useful as a dental implement, comprising a housing formed with a bore, a stem displaceable within the bore, a fingerpiece coupled to one end of the stem and engageable by the user for displacing the stem within the bore, and the opposite end of the stem through an opening in the housing. The instrument further includes an electrical measuring circuit carried by the housing for measuring the displacement of the opposite end of the stem and a display for displaying its displacement as measured by the electrical measuring circuit.

The described preferred embodiments, the housing is long and slim, and includes a laterally-extending projection (e.g., an annular flange) enabling the user to hold the housing between two fingers with the two fingers contacting the projection, while the user's thumb presses the fingerpiece to displace the stem. In the described preferred embodiments, the housing further includes a coiled spring urging the fingerpiece and stem to normal positions wherein the stem is within the housing, preferably with its tip flush with the end of the housing.

Two embodiments of the invention are described below for purposes of example.

One described embodiment is a dental probe for measuring the depth of dental pockets. In this described embodiment, the opposite end of the stem includes a probe tip which is tapered so as to be insertable into the dental pocket to measure its depth; in addition, the housing a formed with a right-angle bend at the end having the opening through which the probe tip is displaceable.

A second embodiment is described, wherein the dental implement is used for measuring the mobility of a tooth. In this described embodiment, the housing is formed with an extension depending below the stem and engageable with the patient's gingiva when the stem is displaced to measure the mobility of the tooth.

The display in the described preferred embodiment is a digital display and is carried by the housing adjacent the end including the fingerpiece. The electrical measuring circuit described includes a linear transducer producing an analog output, and an analog-to-digital converter for converting the analog output to a digital value. The electrical circuit further includes a storage device for storing the value measured by the measuring circuit, and a reset button for resetting the storage device.

Such a instrument can be used in a very convenient manner for making and reading accurate measurements. The invention is thus particularly useful as a dental implement for measuring the depth of a dental pocket, or for measuring the mobility of a tooth.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
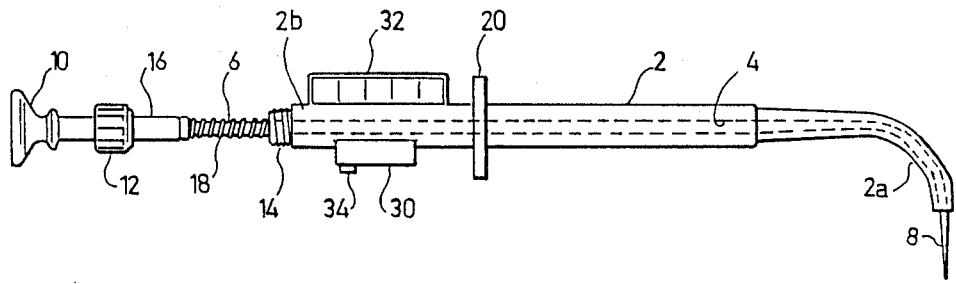
FIG. 1 illustrates one form of measuring instrument constructed in accordance with the present invention.

The measuring instrument illustrated in FIG. 1 of the drawings is designed particularly as a dental probe for measuring the depth of gingival and periodontal pockets, and the like. It includes a housing, generally designated 2, of a long, slim tubular configuration and having a right-angle bend 2a at one end. Housing 2 is formed with a longitudinal bore 4 extending completely through the housing from its bent end 2a to its opposite end 2b. A stem 6 is received within bore 4 and extends from the bent end 2a through its opposite end 2b. Stem 6, or at least that part of it received within bent end 2a of the housing, is flexible to enable it to assume the curvature of the bent end of the housing, but is substantially non-compressible so that displacement of the end of the stem projecting through housing end 2b will produce an equal displacement of the opposite end of the stem. Stem 6 may be a solid rod or wire of a suitable plastic or metal.

A probe tip 8 is secured to the end of stem 6 within the housing bent portion 2a. Probe tip 8 is of metal, e.g., stainless steel, and is of a tapered construction, decreasing in diameter to its outer tip. For example, the probe may be about 10 mm in length, decreasing in diameter from 1 mm to 0.5 mm.

A fingerpiece 10 is attached to the housing end 2b by means of a collar 12 threadedly received on threads 14 formed in the housing. Fingerpiece 10 includes an extension 16 engageable with the end of stem 6 such that when collar 12 is secured to the housing 2, pressing fingerpiece 10 will displace the stem. A coiled spring 18 is disposed within the housing, when collar 12 is attached thereto, and urges the fingerpiece 10 and stem 6, as well as the probe tip 8 at the opposite end of the stem, to a normal, non-displaced position, wherein the probe tip 8 is retracted within the housing, preferably with its tip flush with the respective end of the housing.

To facilitate displacement of fingerpiece 10, the housing is formed with an annular projection or flange 20 extending laterally of the housing. Thus, the user may conveniently support the housing between two fingers with the two fingers engaging the side of flange 20 facing the probe tip 8, and with the thumb engaging the fingerpiece 10, in the manner of holding a conventional syringe.

The illustrated device further includes an electrical measuring circuit, generally designated 30, for measuring the displacement of the probe tip 8, a display 32 for displaying the displacement of the probe tip, and a reset button 34 which enables the user to reset the measurement made and displayed. The foregoing elements of measuring circuit 20 are carried by the housing between its annular flange 20 and fingerpiece 10.

Figure 2:
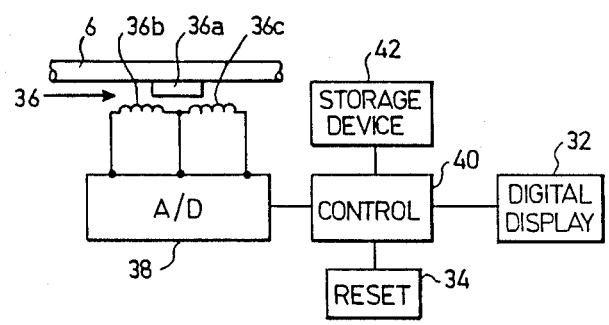
FIG. 2 is a block diagram illustrating the electrical circuit included in the measuring instrument of FIG. 1.

An example of an electrical circuit that may be used is shown in FIG. 2. It includes a linear transducer 36, which produces an analog output, an analog-to-digital converter 38 for converting the analog to a digital value, a control circuit 40, and a storage device 42 for storing the digital value measured by the electrical circuit. This digital value is displayed in the digital display 32, preferably providing a display from both sides of the instrument. The previously mentioned reset button 34 is depressed whenever it is desired to erase the measurement made and displayed in display 32 in order to make another measurement.

The linear transducer 36 illustrated in FIG. 2 may be of the variable reluctance type. It includes a core 36a fixed to stem 6 so as to be movable therewith and is inductively coupled to a pair of windings 36b, 36c producing an output which is substantially linear with respect to the displacement of stem 6. Such a transducer produces a substantial linear output over the complete movement of stem 6, and thereby of the probe tip 8. The circuit may be operated by a battery included within the measuring circuit 30.

It will be appreciated, however, that other forms of measuring circuits and transducers could be used, e.g., transducers which produce a digital output directly thereby obviating the need for the analog-to-digital converter 38.

The manner of using the dental probe illustrated in the drawings will be apparent from the above description.

Thus, the dentist, or other dental attendant using the probe, holds the probe between two fingers, with the two fingers bearing against the annular flange 20, and the thumb bearing against fingerpiece 10, similar to the manner of holding a conventional syringe 10. The user then introduces the probe into the patient's mouth with the portion of the probe from the annular flange 20 to the fingerpiece 10 being external of the patient's mouth. The user may manipulate the probe, and particularly the tip 8, in the conventional manner.

Whenever a measurement is to be taken, e.g., to measure the depth of a gingival or periodontal pocket, the end 2a of the housing is placed on the gingival surface adjacent to the tooth, with the probe tip 8 aligned with the pocket, and fingerpiece 10 is depressed until the probe tip engages the bottom of the pocket to be measured. This becomes evident by the resulting resistance to further displacement of the stem and probe tip. The magnitude of displacement of the stem 6 is converted by transducer 36 to an electrical value. This value is stored in storage device 42 and is also displayed in the digital display 32, so that the user can easily read the measurement taken. Whenever the measurement is to be erased, this can be done by depressing reset button 34, thereby resetting the storage device 42 and the digital display 32.

Figure 3:
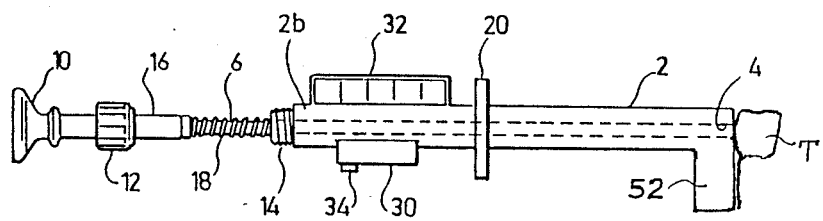
FIG. 3 illustrates another form of measuring instrument constructed in accordance with the present invention.

FIG. 3 illustrates another dental implement constructed in accordance with the invention for measuring the mobility of a tooth, namely tooth T. The implement illustrated in FIG. 3 includes the same construction as that in FIG. 1, except that the stem end does not have a probe, nor does the housing have a curvature. Instead, the housing 2 is formed with an extension 52 engageable with the gingiva of the tooth whose mobility is to be measured.

When using the tool illustrated in FIG. 3, the dentist places extension 52 against the gingiva aligned with the tooth T where mobility is being measured. The dentist then presses the fingerpiece 10 to project stem 6 through opening 4 into engagement with the tooth T to move it horizontally. The magnitude of movement of the stem, and thereby of tooth T, is measured by the measuring circuit illustrated in FIG. 2 and is displayed in the digital display 32, in the same manner as described above with respect to FIG. 1.

While the invention has been described with respect to one preferred embodiment, it will be appreciated that many variations may be made. For example, other forms of electrical measuring circuits, and/or of transducers, may be used. Also, the control circuit can include circuitry which inverts the digital display, e.g., by pressing a button, when making measurements of the upper teeth. In addition, while in both of the described embodiments, the stem or probe tip is normally retained by spring 18 flush with the end of the housing formed with the opening through which the stem is displaced, it will be appreciated that the stem could normally be held retracted within the housing spaced from its end, and electrical means could be provided to indicate when the stem passes the respective end of the housing to start the measurement of the depth of a dental pocket, or when the stem engages the tooth whose mobility is to be measured. Other variations, modifications and applications of the invention will be apparent.

What is claimed is:

1. A small portable measuring instrument, particularly useful as a dental implement, comprising:
   a housing formed with a bore;
   a stem displaceable within said bore;
   a fingerpiece coupled to one end of the stem and engageable by the user for displacing the stem within the bore and the opposite end of the stem through an opening in the housing;
   said housing being long and slim, and including a laterally-extending projection enabling the user to hold the housing between two fingers with the two fingers contacting the projection, while the user's thumb presses said fingerpiece to displace the stem and probe tip;
   an electrical measuring circuit carried by the housing for measuring the displacement of said opposite end of the stem;

and a display for displaying the displacement of said opposite end of the stem as measured by said electrical measuring circuit.

2. The instrument according to claim 1, wherein said housing further includes a coiled spring urging said fingerpiece and stem to normal positions wherein the stem is within the housing.

3. The instrument according to claim 1, wherein said opposite end of the stem is flush with the end of the housing formed with said opening in the normal non-displaced position of the stem.

4. The instrument according to claim 1, wherein said opposite end of the stem includes a probe tip which is tapered so as to be insertable into a dental pocket to measure the depth of said dental pocket.

5. The instrument according to claim 4, wherein said housing is formed with a right-angle bend at the end thereof having the opening through which the probe tip is displaceable.

6. The instrument according to claim 1, wherein said housing is formed with an extension depending below the stem and engageable with the patient's gingiva when the stem is displaced to measure the mobility of a tooth.

7. The instrument according to claim 1, wherein said display is a digital display and is carried by said housing adjacent the end thereof including said fingerpiece.

8. The instrument according to claim 1, wherein said electrical measuring circuit includes a linear transducer producing an analog output, and an analog- to-digital converter for converting the analog output to a digital value.

9. The instrument according to claim 8, wherein said transducer is a linear variable-reluctance transducer.

10. The instrument according to claim 1, wherein said electrical measuring circuit further includes a storage device for storing the value measured by said measuring circuit, and a reset button for resetting said storage device.

11. A small portable measuring instrument, particularly useful as a dental implement, comprising:
    a housing formed with a bore;
    a stem displaceable within said bore;
    a fingerpiece coupled to one end of the stem and engageable by the user for displacing the stem within the bore and the opposite end of the stem through an opening in the housing;
    a coiled spring urging said fingerpiece and step to normal, non-displaced positions;
    said housing being long and slim, and including a laterally-extending projection enabling the user to hold the housing between two fingers with the two fingers contacting the projection, while the user's thumb presses said fingerpiece to displace the stem and probe tip;
    an electrical measuring circuit carried by the housing for measuring the displacement of the probe tip;
    and a display for displaying the displacement of the probe tip as measured by said electrical measuring circuit.

12. The instrument according to claim 11, wherein said opposite end of the stem is flush with the end of the housing formed with said opening in the normal, non-displaced position of the stem.

13. The instrument according to claim 11, wherein said opposite end of the stem includes a probe tip which is tapered so as to be insertable into a dental pocket to measure the depth of said dental pocket.

14. The instrument according to claim 13, wherein said housing is formed with a right-angle bend at the end thereof having the opening through which the probe tip is displaceable.

15. The instrument according to claim 11, wherein said housing is formed with an extension depending below the stem and engageable with the patient's gingiva when the stem is displaced to measure the mobility of said first tooth.

16. The instrument according to claim 11, wherein said electrical measuring circuit includes a linear transducer producing an analog output, and an analog- to-digital converter for converting the analog output to a digital value, and wherein said display is a digital display and is carried by said housing adjacent the end thereof including said fingerpiece.

17. The instrument according to claim 16, wherein said electrical measuring circuit further includes a storage device for storing the value measured by said measuring circuit, and a reset button for resetting said storage device.

* * * * *